United States Patent [19]

Itoh et al.

[11] Patent Number: 5,449,587

[45] Date of Patent: * Sep. 12, 1995

[54] COMPACT DISK-WRITE ONCE TYPE OPTICAL RECORDING MEDIA

[75] Inventors: Hisato Itoh; Takahisa Oguchi, both of Yokohama; Katashi Enomoto, Zushi; Tsutomu Nishizawa, Yokohama, all of Japan

[73] Assignees: Mitsui Toatsu Chemicals, Incorporated, Tokyo; Yamamoto Chemicals, Incorporated, Yao, both of Japan

[*] Notice: The portion of the term of this patent subsequent to Jun. 23, 2009 has been disclaimed.

[21] Appl. No.: 192,793

[22] Filed: Feb. 7, 1994

Related U.S. Application Data

[63] Continuation of Ser. No. 680,921, Apr. 5, 1991, abandoned, which is a continuation-in-part of Ser. No. 451,175, Dec. 15, 1989, Pat. No. 5,124,067.

[30] Foreign Application Priority Data

| Dec. 15, 1988 | [JP] | Japan | 63-314986 |
| Jan. 13, 1989 | [JP] | Japan | 1-4763 |
| Jan. 13, 1989 | [JP] | Japan | 1-4764 |
| Apr. 19, 1989 | [JP] | Japan | 1-97604 |
| Apr. 7, 1990 | [JP] | Japan | 2-91361 |

[51] Int. Cl.$^6$ ............................. G11B 7/24
[52] U.S. Cl. ............. 430/273; 430/275; 430/495; 430/945; 430/270; 369/284; 369/288; 346/135.1
[58] Field of Search ........... 430/270, 495, 956, 273, 430/275; 369/288, 284; 346/135.1; 540/139, 140; 252/587

[56] References Cited

U.S. PATENT DOCUMENTS

| 4,529,688 | 7/1985 | Law et al. | 430/495 |
| 4,788,128 | 11/1988 | Barlow | 346/135.1 |
| 4,798,781 | 1/1989 | Hirose et al. | 346/135.1 |
| 4,873,131 | 10/1989 | Kashima et al. | 346/153.1 |
| 4,943,681 | 7/1990 | Sato et al. | 346/135.1 |
| 4,946,762 | 8/1990 | Albert et al. | 346/135.1 |
| 4,996,089 | 2/1991 | Saito et al. | 430/945 |
| 5,024,926 | 6/1991 | Itoh et al. | 430/495 |
| 5,079,135 | 1/1992 | Matsuzawa et al. | 346/135.1 |
| 5,090,009 | 2/1992 | Hamada et al. | 369/284 |
| 5,124,067 | 6/1992 | Itoh et al. | 252/587 |
| 5,132,153 | 7/1992 | Hirose et al. | 430/945 |
| 5,137,798 | 8/1992 | Duggan et al. | 430/270 |

FOREIGN PATENT DOCUMENTS

| 0337209 | 10/1929 | European Pat. Off. . | |
| 0302497 | 2/1989 | European Pat. Off. . | |
| 2455675 | 5/1975 | Germany | 540/140 |
| 85630 | 7/1975 | Japan . | |
| 46019 | 4/1978 | Japan . | |
| 37851 | 3/1983 | Japan . | |
| 183296 | 10/1983 | Japan . | |
| 61-223056 | 10/1986 | Japan | 540/139 |
| 159842 | 6/1989 | Japan . | |
| 1198391 | 8/1989 | Japan | 430/495 |

OTHER PUBLICATIONS

J. Org. Chem., vol. 27, pp. 2037–2039 (1962).
J. Org. Chem., vol. 6, pp. 852–857 (1941).
J. Chem. Soc., Perkin Trans. I, pp. 2453–2458 (1988).

*Primary Examiner*—Charles L. Bowers, Jr.
*Assistant Examiner*—Martin Angebrannet
*Attorney, Agent, or Firm*—Oblon, Spivak, McClelland, Maier & Neustadt

[57] ABSTRACT

The invention discloses a CD-WO type optical recording medium which has a constitution obtained by successively laminating a recording layer, a metal reflection layer and a protective layer; is prepared by using in the recording layer a colorant having a melting point of 150° to 300° C., decomposition initiating temperature of 200° to 350° C., and λ max of 720 nm; and has high sensitivity, low recording distortion and high durability. The colorant can be enhanced its effect by introducing halogen atoms.

2 Claims, No Drawings

COMPACT DISK-WRITE ONCE TYPE OPTICAL RECORDING MEDIA

This application is a continuation of application Ser. No. 07/680,921, filed Apr. 5, 1991, now abandoned, which is a continuation-in-part of application Ser. No. 07/451,175, filed Dec. 15, 1989, now U.S. Pat. No. 5,124,067.

BACKGROUND OF THE INVENTION

1. Field of the Invention

The present invention relates to an optical recording medium used for recording and storage of information.

2. Description of the Related Art

Conventionally, Compact Disk-Write Once type (hereinafter referred to as CD-WO) optical recording media obtained by laminating on a substrate a recording layer (optical absorption layer), an optical reflection layer and a protective layer have been known in Japanese Laid-Open Patent 183296 (1983), 46019 (1978), 37851 (1983) and 159842 (1989).

However, copper phthalocyanine (Trade mark; OLEOSOLE FAST BLUE EL, manufactured by SUMITOMO CHEMICAL CO., LTD.) which constitutes the recording layer (optical absorption layer) in the optical recording medium disclosed in Japanese Laid-Open Patent 183296 (1983) could not provide sensitivity required for the optical recording media.

The medium of Example 2 in Japanese Laid-Open Patent 46019 (1978) was poor in sensitivity and durability, and did not satisfy reflectance of 65% or more in a wavelength of 780 to 830 nm, which condition is required for the optical recording media, CD-WO in particular.

Japanese Laid-Open Patent 37851 (1983) disclosed the same constitution as that of the present invention. However, the reflectance of optical recording media obtained in the examples was 30 to 51% and lower than the reflectance of 65% which was required for CD-WO. Durability was also unsatisfactory.

As illustrated in Japanese Laid-Open Patent 159842 (12989), the medium prepared by using a common cyanine colorant described in, for example, Photosensitive Dye Table published by Japan Photosensitive Dye Research Institute (1969), led to insufficient sensitivity or reflectance lower than 65%.

The cyanine colorant disclosed in the examples of EP 353,394 and the phthalocyanine colorant disclosed in the examples of EP 353,393 had poor sensitivity and signal property, and were unsuitable as the colorant for the CD-WO type optical recording media.

3. Summary of the Invention

The object of the invention is to provide a novel CD-WO type optical recording medium having reflectance of 65% or more which has not been obtained in abovementioned conventional examples.

As a result of an intensive investigation in order to accomplish the above object, the present inventors have found that, when the recording layer of the CD-WO type optical recording medium contains a near infrared absorber having a melting point of from 150° to 300° C. and a decomposition initiating temperature of from 200° to 350° C., the optical recording medium constituted of the recording layer containing the near infrared absorber has high sensitivity for writing signals, good symmetry of written signals and small distortion in recording.

The present inventors have further found that, when the recording layer contains a near infrared absorber having a maximum absorption wavelength ($\lambda$ max) of from 670 to 720 nm using carbon tetrachloride, chloroform or toluene as a solvent, the medium can maintain its reflectance at 65% or more. Thus the present invention has been completed. With respect to the melting point and decomposition initiating temperature of the near infrared absorber used in particular, introduction of halogen atoms or specific substituents has also been found to be effective for achieving the object.

The present inventors have found that particularly the melting point and the decomposition initiating temperature have great contribution to the sensitivity in recording and stability in regeneration, and completed the invention on the basis of the discovery.

The optical recording media of the invention have a constitution obtained by successively laminating the recording layer, a metal reflection layer and a protective layer on a transparent substrate. The above recording layer is characterized by containing the near infrared absorber composed of a compound or a mixture of the same having a melting point in the range of from 150° to 300° C. and a decomposition initiating temperature in the range of from 200° to 350° C.

The melting point was measured with a common melting point tester. The decomposition initiating temperature was measured with a differential thermal-thermogravimetric simultaneous analyzer (DTA-TGA). The temperature of 5% decomposition was defined as the decomposition initiating temperature.

DETAILED DESCRIPTION OF THE PREFERRED EMBODIMENTS

The substrate which can be used for the optical recording media of the present invention is an optically transparent resin. Exemplary resins for use in the substrate include acrylic resin, polyethylene resin, polyvinyl chloride resin, polyvinylidene chloride resin, polycarbonate resin, ethylene resin, olefine copolymer resin, vinyl chloride copolymer resin, vinylidene chloride copolymer resin and styrene copolymer resin. The substrate can be treated with a thermosetting resin or an ultraviolet curing resin on its surface.

The near infrared absorbers which can be contained in the recording layer include, for example, phthalocyanine compounds and isomers of the same which are represented by the formula (I):

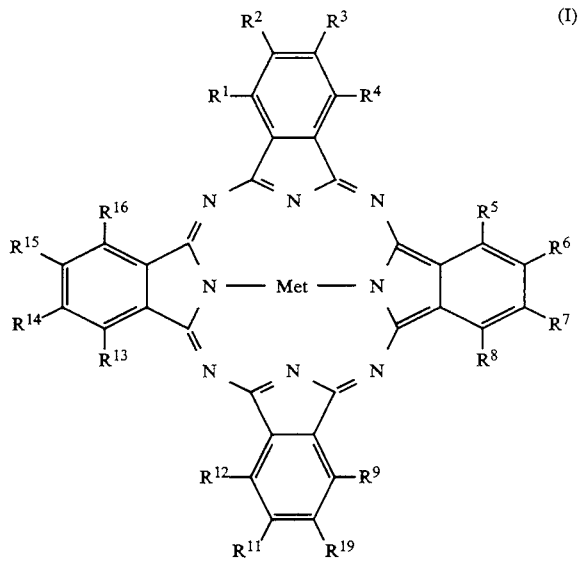

(I)

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are individually a hydrogen atom, halogen atom, nitro, substituted or unsubstituted alkyl, substituted or unsubstituted aryl, substituted or unsubstituted alkoxy, substituted or unsubstituted aryloxy, substituted or unsubstituted alkylthio, or substituted or unsubstituted arylthio group; wherein, in a combination of $R^1$ and $R^4$, $R^5$ and $R^8$, $R^9$ and $R^{12}$, and $R^{13}$ and $R^{16}$, at least one of the combination is selected from a substituted or unsubstituted alkoxy, substituted or unsubstituted aryloxy, substituted or unsubstituted alkylthio, and substituted or unsubstituted arylthio group; in $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$, from 1 to 4 groups are halogen atoms; and Met is two hydrogen atoms, a divalent metal atom, or a trivalent or tetravalent metal derivative; and also include cyanine colorants, anthraquinone colorants, polyolefine colorants and thiapyrylium colorants. The optical recording media having excellent recording sensitivity and recording properties can be obtained by selecting from these substances a colorant or a mixture of the same having a melting point of from 150° to 300° C. and a decomposition initiating temperature of from 200° to 350° C.

The recording layers of the media preferably comprise a near infrared absorber having a maximum absorption wavelength (λ max) in the range of from 670 to 720 nm in a chloroform solution to improve recording and regeneration properties. Hence, the recording message can be regenerated by mean of a compact disk regenerating player or CD-ROM regenerating device which are on the market, i.e., by mean of a semiconductor laser having a wavelength of from 760 to 800 nm. The near infrared absorber having a maximum molar extinction coefficient (λ max) of $1 \times 10^5$ $1\,mol^{-1}cm^{-1}$ or more at the maximum absorption wavelength in the chloroform solution is particularly preferred in view of sensitivity and regeneration.

The recording layer can be prepared by coating or vapor-depositing the above single compound or a mixture of the same into one or two layers. In a coating method, 20% by weight or less, preferably 0% by weight of a binder resin and from 0.05 to 20% by weight, preferably from 0.5 to 20% by weight of the above compound are dissolved in a solvent, and the resulting solution is coated with a spin coater. Vapor deposition method is carried out by depositing the above compound on the substrate under $10^{-5}$ to $10^{-7}$ torr at 100° to 300° C.

The thickness of the recording layer containing the near infrared absorber is preferably from 50 to 300 nm.

The solvent which can be used for the spin coating depends upon the solvent resistance of the substrate. Preferred solvents include, for example, halogenated hydrocarbons such as dichloromethane, chloroform, carbon tetrachloride, tetrachloroethylene and dichlorodifluoroethane; ethers such as diethyl ether, dipropyl ether and dibutyl ether; alcohols such as methanol, ethanol and propanol; cellosolves such as methyl cellosolve and ethyl cellosolve; and hydrocarbons such as hexane, cyclohexane, octane, benzene and toluene.

Materials used for the reflection layer include aluminum and gold. Preferred protective layer is a transparent photo-setting or thermosetting type resin.

The optical reflection layer is prepared by vapor deposition method and sputtering method. The thickness of the optical reflection layer is preferably from 1 to 100 nm.

The protective layer is prepared by applying an ultraviolet curing resin or thermosetting resin with a spin coating method and curing the resin. The thickness of the protective layer is preferably from 1 to 500 μm.

Preparation of the optical recording media is preferably carried out by using polycarbonate or polyacrylate as a substrate and applying with a spin coating method in view of cost and easiness in handling by customers.

The present invention will hereinafter be illustrated in detail by way of examples. However, these examples are not to be construed to limit the scope of the invention. Part in the examples means part by weight.

EXAMPLE 1

One part of palladium 4,8,12,16-tetrabromo-1,5,9,13-tetra (1,3-dimethylbutyloxy)phthalocyanine having a melting point of 150°–180° C., decomposition initiating temperature of 280° C., λ max of 703 nm and ε max of $1.6 \times 10^5$ $1\,mol^{-1}\,cm^{-1}$ was dissolved in 200 parts of dibutyl ether and coated on a polycarbonate optical disk substrate. Gold was vapor deposited on the coated surface and successively over coated with a photo-setting type polyacrylate resin and the resin was cured. The optical disk thus obtained had a C/N ratio of 60 dB at a linear velocity of 1.4 m/sec under laser power of 7 mW, that is, sensitivity was good. After irradiating in a fademeter at 63° C. for 100 hours, no deterioration was observed on the recording layer.

EXAMPLE 2

Ten parts of palladium tetra(1,3-dimethylpropyloxy)phthalocyanine was dissolved in 1000 parts of carbon tetrachloride. Two parts of bromine were added dropwise to the solution at 40° C. and reacted for 3 hours. Precipitated crystals were filtered, washed and dried to obtain 5 parts of a colorant mixture of the formula:

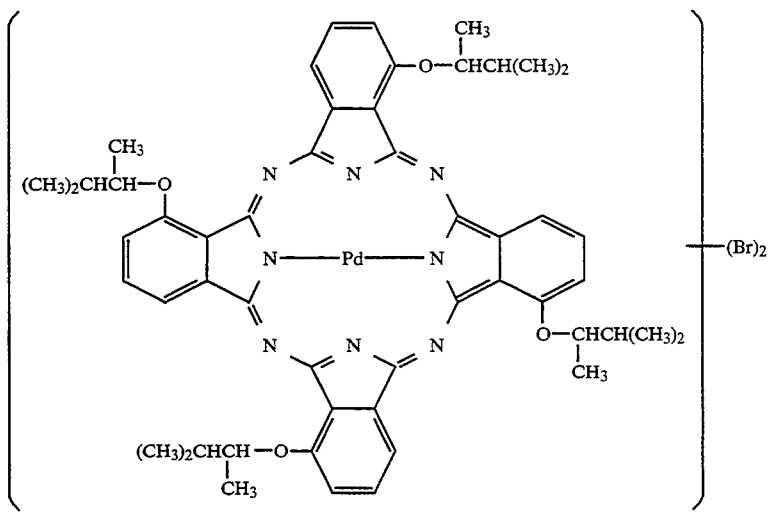

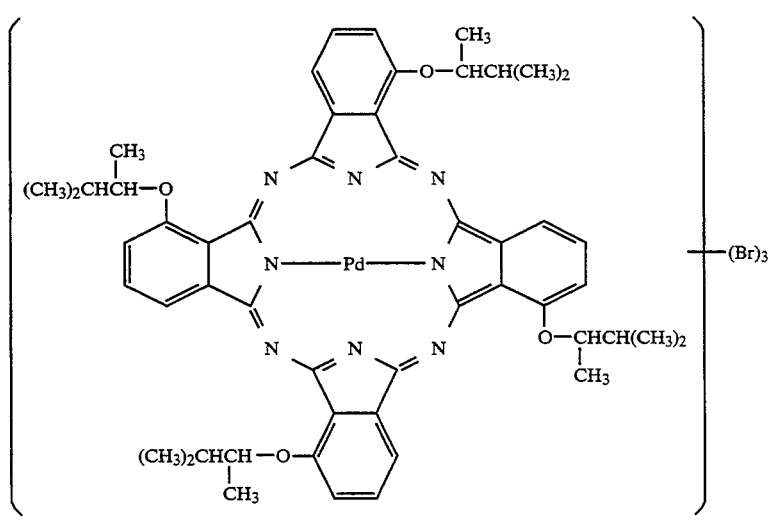

The colorant mixture had a melting point of 170° to 200° C. and a decomposition initiating temperature of 305° C.

A solution obtained by dissolving 5 parts of the mixture in 500 parts of n-octane was coated with a spin coater on a polycarbonate substrate for CD-WO to obtain a dried film thickness of 150 nm. Gold was sputtered on the coated surface to obtain a film thickness of 30 nm and successively an ultraviolet curing resin was coated on the gold layer to form a protective layer by curing the resin.

The CD-WO type medium thus obtained had a reflection of 65%, and could be written a record having a C/N ratio of 65 dB at a linear velocity of 1.4 m/sec with a laser beam of 7 mW in power and 790 nm in wavelength. The recording medium had no change after a light resistance test with a carbon-arc lamp at 63° C. for 200 hours.

EXAMPLE 3

Ten parts of palladium 1,5,9,13-tetra(2,4,4-trimethyl-3-hexyloxy)phthalocyanine was dissolved in 1000 parts of acetic acid, and 10 parts of iodine were added and reacted at 50° C. for 3 hours. Precipitated crystals were filtered and purified to obtain a colorant mixture illustrated by the formula:

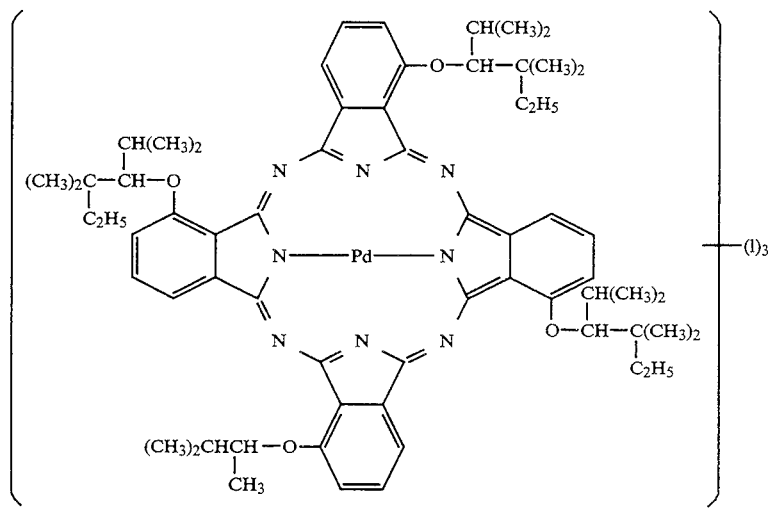

The mixture had a melting point of 200° to 245° C., decomposition initiating temperature of 285° C., λ max of 708 nm and ε max of $1.5 \times 10^5$ l $mol^{-1}$ $cm^{-1}$.

A solution obtained by dissolving 5 parts of the colorant mixture in n-octane was coated on a polycarbonate substrate for CD-WO with a spin coater to obtain a film thickness of 120 nm. Gold was vapor deposited on the coated layer to a thickness of 50 nm and successively a protective layer was formed by using an ultraviolet curing resin.

The CD-WO medium thus obtained was written a record at a linear velocity of 1.3 m/sec with a laser of 7 mW in power and 780 nm in wavelength to obtain the record having a C/N ratio of 55 dB. The recording medium had no change after a light resistance test with a xenon lamp at 50° C. for 200 hours.

EXAMPLE 4

A solution was prepared by dissolving 5 parts of phthalocyanine which is illustrated by the above formula and has a melting point of 165° to 200° C. and a decomposition initiating temperature of 295° C., in 300 parts of a 3:1 mixture of dibutyl ether and diisopropyl ether. The solution was coated with a spin coater on a PMMA substrate for CD-WO to a thickness of 120 nm. Gold was successively sputtered to a thickness of 20 nm and finally a protective layer was formed with an ultraviolet setting resin.

The recording medium thus obtained was written a record at a linear velocity of 1.4 m/sec with a laser of 8 mW in power and 780 nm of wavelength to obtain the record having a C/N ratio of 60 dB.

EXAMPLE 5

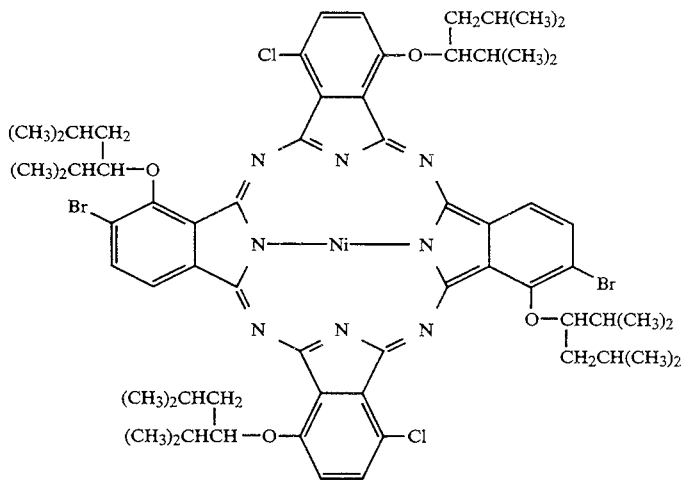

(A)

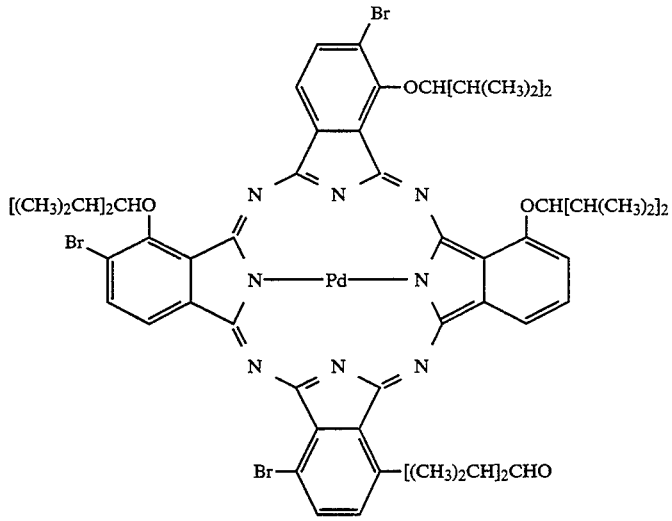

(B)

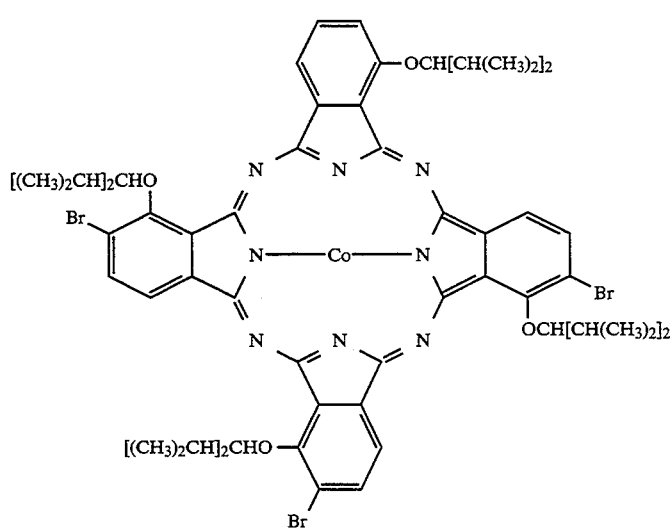

A 1:1 mixture of above illustrated compounds (A) and (B) which has a melting point of 230° to 240° C., decomposition initiating temperature of 270° C., λ max of 710 nm and ε max of $1.7 \times 10^5$ l mol$^{-1}$ cm$^{-1}$ was used. The procedures of Example 1 were repeated to obtain a CD-WO type optical recording medium.

The recording medium was recorded at a linear velocity of 1.4 m/sec with a laser of 8 mW in power and 780 nm in wavelength to obtain the record having a C/N ratio of 55 dB.

EXAMPLE 6

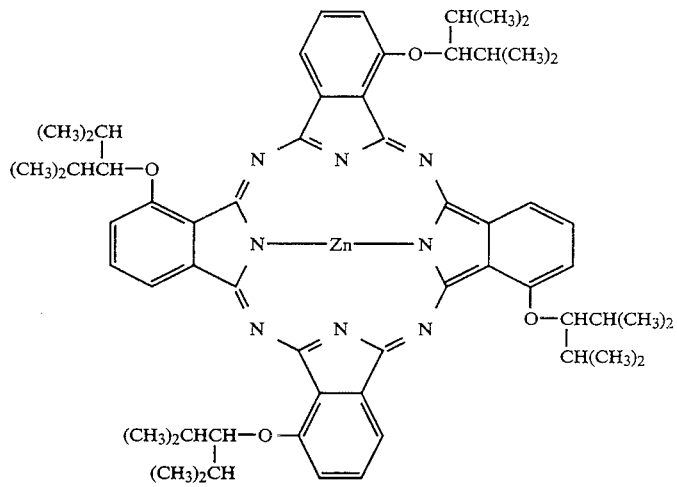

A solution was prepared by dissolving 5 parts of the phthalocyanine illustrated by the formula (melting point; 195°–225° C., decomposition initiating temperature; 253° C., λ max; 707 nm and ε max of $2.0 \times 10^5$ $l\ mol^{-1} cm^{-1}$) in 300 parts of dibutyl ether. The solution was coated with a spin coater on a polycarbonate substrate for CD-WO to a thickness of 150 nm. Gold was successively sputtered to a thickness of 30 nm and finally a protective layer was formed with an ultraviolet curing resin.

The medium thus obtained was written at a linear velocity of 1.3 m/sec with a laser of 8 mW in power and 780 nm in wavelength to obtain a record having a C/N ratio of 60 dB.

The medium obtained was recorded at a linear velocity of 1.4 m/sec, with a laser of 7 mW in power and 780 nm in wavelength to obtain a record having a C/N ratio of 55 dB.

EXAMPLE 7

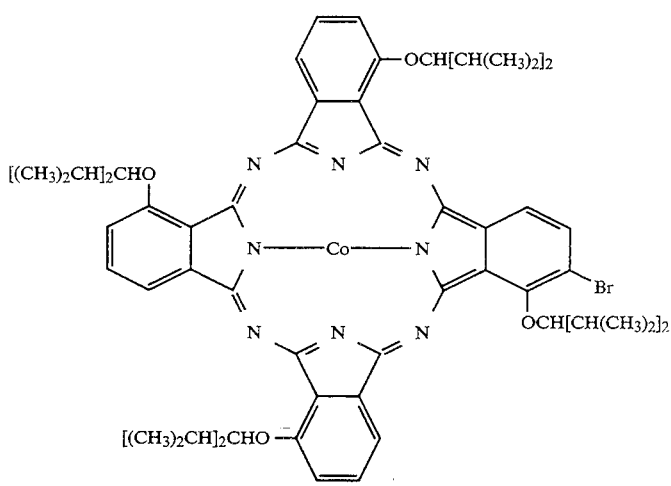

Five parts of the phthalocyanine illustrated by the formula and having a melting point of 250° C. or above, decomposition initiating temperature of 309° C., λ max of 694 nm and ε max of $1.7 \times 10^5$ $l\ mol^{-1}\ cm^{-1}$ were dissolved in 300 parts of chloroform. The solution obtained was coated on a substrate which was previously grooved the surface by treating with an acrylic base photo-polymer. The same procedures as described in Example 6 was carried out to obtain an optical recording medium.

EXAMPLE 8

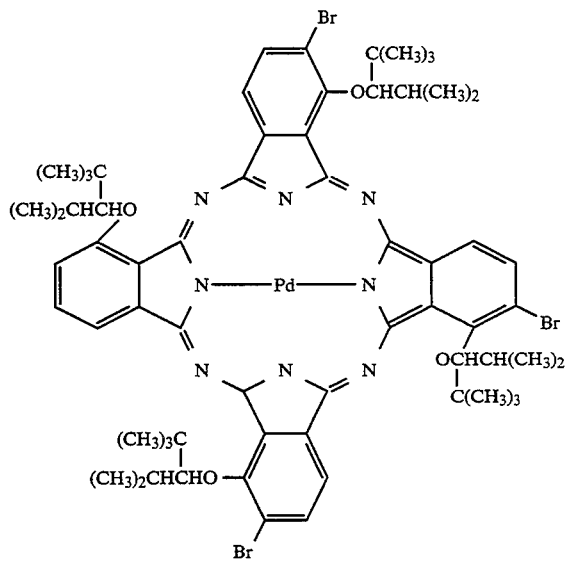

The phthalocyanine illustrated by the formula and having melting point of 262° to 286° C., decomposition initiating temperature of 310° C., λ max of 708 nm and ε max of $1.8 \times 10^5$ $1$ $mol^{-1}$ $cm^{-1}$ was used. The procedures described in Example 6 were repeated to prepare a CD-WO type optical recording medium.

The medium obtained was written at a linear velocity of 1.4 m/sec with a laser of 7 mW in power and 780 nm wavelength to obtain a record having a C/N ratio of 57 dB.

EXAMPLE 9

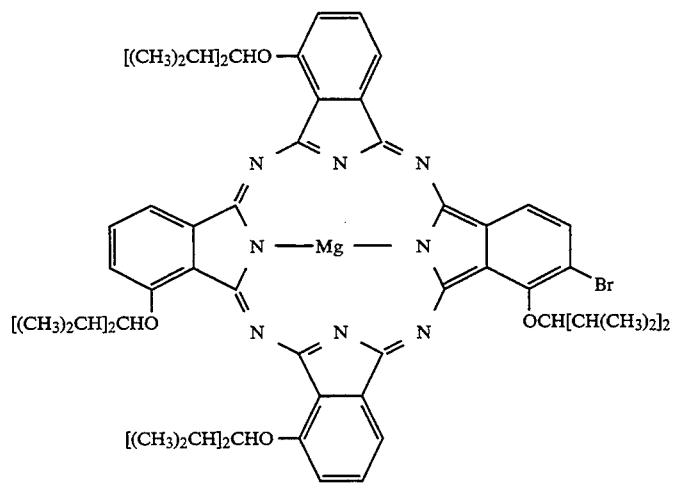

The phthalocyanine illustrated by the formula and having a melting point of 225° to 245° C., decomposition initiating temperature of 289° C., λ max of 706 nm and ε max of $1.8 \times 10^5$ $1$ $mol^{-1}$ $cm^{-1}$ was used.

The same procedures as described in Example 6 were carried out to prepare a CD-WO type optical recording medium.

The medium obtained was recorded at a linear velocity of 1.3 m/sec with a laser of 7 mW in power and 780 nm in wavelength to obtain a record having a C/N ratio of 62 dB.

EXAMPLE 10

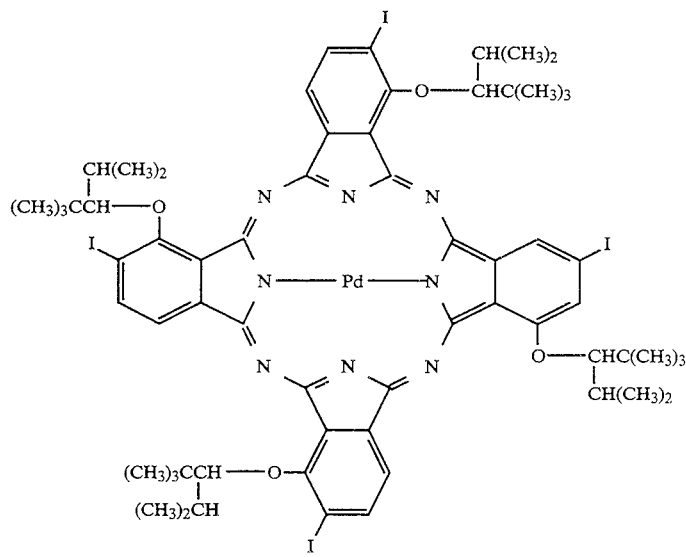

The phthalocyanine illustrated by the formula and having a melting point of 280° to 292° C. decomposition initiating temperature of 294° C., λ max of 707 nm and ε max of $1.9 \times 10^5$ 1 mol$^{-1}$ cm$^{-1}$ was used. The same procedures as described in Example 6 were carried out to prepare a CD-WO type optical recording medium.

The medium obtained was written at a linear velocity of 1.4 m/sec with a laser of 7 mW in power and 780 nm in wavelength to obtain a record having a C/N ratio of 61 dB.

COMPARATIVE TEST

The above obtained CD-WO type optical recording media of the invention were compared their performance with optical recording media prepared by using known conditions. The media prepared in Examples 2, 4 and 5 were used as the media of the invention. The media prepared according to 7 known cases described below were used as comparative examples.

COMPARATIVE EXAMPLE 1

The recording layer contains silver nitrate according to Japanese Laid-Open Patent 37851 (1983).

COMPARATIVE EXAMPLE 2

The following colorant was used according to Japanese Laid-Open Patent 159842 (1989).

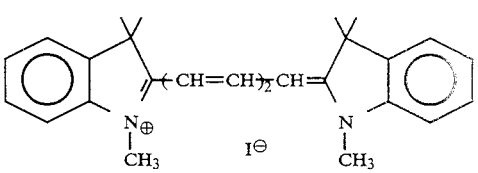

COMPARATIVE EXAMPLE 3

Inorganic compound was used in the recording layer according to Japanese Laid-Open Patent 46019 (1978).

COMPARATIVE EXAMPLE 4

Copper phthalocyanine colorant was used according to Japanese Laid-Open Patent 183296 (1983).

COMPARATIVE EXAMPLE 5

A medium was prepared by carrying out the same procedures as described in Example 1 except that the colorant of the formula having a melting point of 80° to 90° C. and a decomposition initiating temperature of 310° C. was used.

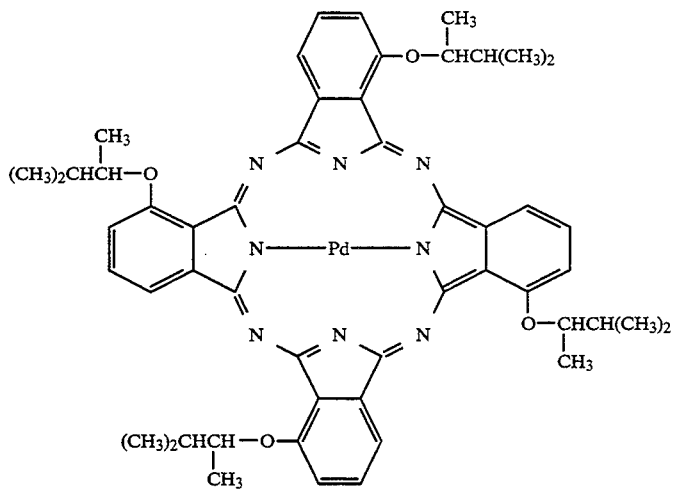

COMPARATIVE EXAMPLE 6

The colorant illustrated by the formula:

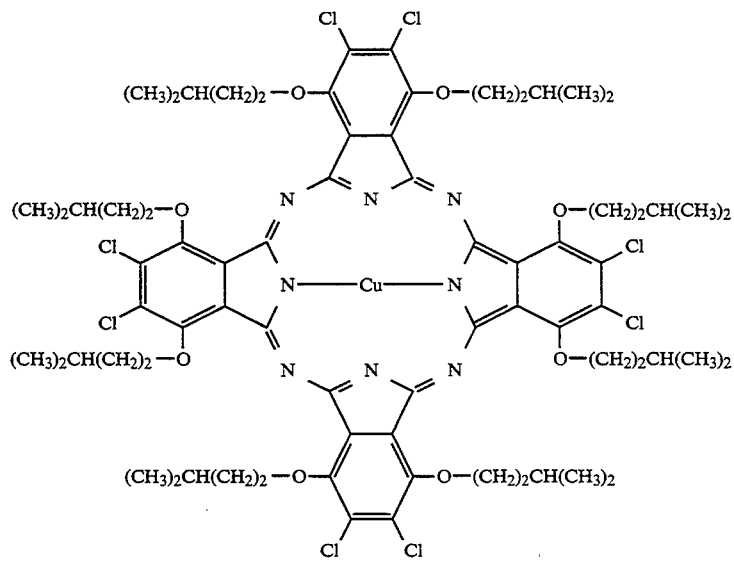

which has a melting point of higher than 250° C. and a decomposition initiating temperature of 305° C. was used. A medium was prepared by carrying out the same procedures as described in Example 1.

COMPARATIVE EXAMPLE 7

The compound illustrated by the formula was used according to EP 353,393.

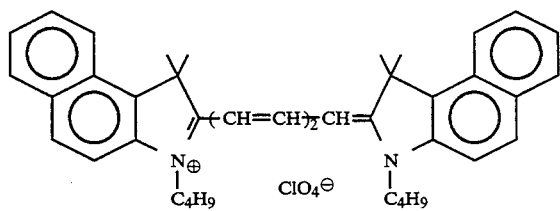

The compound had a melting point of 145° to 148° C. and a decomposition initiating temperature of 210° C.

In the above comparative examples, properties of the media obtained were measured by the following methods. Results were compared with those obtained by examples and summarized in Table 1. Evaluation was made by the following standards.

Reflectance . . . measured with a light beam having a wavelength of 780 nm

Sensitivity . . . measured at a linear velocity of 1.4 m/sec and a wavelength of 780 nm Symmetry . . . measured at a recording power ranging from 5 to 90 mW ◯ . . . less than 5% fluctuation X . . . more than 5% fluctuation Pulse duration correction . . . Necessary correction range was measured by writing 4T signal (231×4=924 nsec) ◯ . . . correction range: 0 to −100 nsec Δ . . . correction range: −100 to −200 nsec X . . . correction range: more than −200 nsec Record distortion . . . Distortion of recorded waveform was measured with an oscilloscope. Distortion of gold layer was examined by observing recording pit under microscope ◯ . . . no distortion X . . . distortion found Durability... measured by variation in record (stability of regenerated light) after reading out $10^5$ times at a linear velocity of 1.4 m/sec with power of 0.5 mW and by variation of record after a daylight exposure fastness acceleration test with a xenon lamp at 40° C. for 100 hours ◯ ... Each variation is less than 10%. Δ ... Each variation is from 10 to 20%. X ... Each variation is more than 20%.

the near-infrared absorber consisting essentially of a phthalocyanine or a mixture of phthalocyanines having a melting point in the range of from 150° to 300° C., a decomposition initiating temperature in the range of from 200° to 350° C., a maximum absorption wavelength of from 670 to 720 nm in chloroform solution and a maximum molar extinction coefficient of $1 \times 10^5$ l mol$^{-1}$ cm$^{-1}$ or more at the maximum absorption wave-

TABLE 1

| Medium | Reflectance (%) | Sensitivity (mW/dB) | Symmetry | Pulse duration correction | Record distortion | Durability | Melting point (°C.) | Decomp. init. temperature* (°C.) | λ max (nm) | ε max (l mol$^{-1}$ cm$^{-1}$) |
|---|---|---|---|---|---|---|---|---|---|---|
| Example 2 | 65 | 7/60 | ○ | ○ | ○ | ○ | 170–200 | 305 | 700 | $1.6 \times 10^5$ |
| Example 4 | 70 | 9/55 | ○ | ○ | ○ | ○ | 165–200 | 295 | 709 | $1.7 \times 10^5$ |
| Example 5 | 65 | 7/60 | ○ | ○ | ○ | ○ | 230–240 | 270 | 710 | $1.7 \times 10^5$ |
| Comp. Ex. 1 | 44 | 10/40 | X | X | X | Δ | —** | — | — | |
| Comp. Ex. 2 | 70 | 12/55 | X | X | X | Δ | — | 220 | 741 | |
| Comp. Ex. 3 | 70 | 12/50 | X | X | X | Δ | —** | — | — | |
| Comp. Ex. 4 | 72 | 15/50 | X | X | X | ○ | >300 | 505 | 670 | |
| Comp. Ex. 5 | 62 | 15/50 | X | X | X | ○ | 80–90 | 310 | 690 | |
| Comp. Ex. 6 | 40 | 6/30 | X | X | X | X | >250 | 305 | 739 | |
| Comp. Ex. 7 | 70 | 7/50 | X | X | X | X | 145–148 | 210 | 680 | |

Note:
*Measured by TG-DTA
**No data because of inorganic medium

What is claimed is:

1. A compact disk-write once type optical recording medium having a constitution obtained by successively laminating a recording layer, a metal reflection layer and a protective layer on a transparent substrate, said recording layer comprising a near-infrared absorber, length in the chloroform solution.

2. The optical recording medium of claim 1 wherein the recording layer comprises the near infrared absorber having from 1 to 4 halogen atoms in a molecule.

* * * * *

UNITED STATES PATENT AND TRADEMARK OFFICE
CERTIFICATE OF CORRECTION

PATENT NO.  : 5,449,587
DATED       : September 12, 1995
INVENTOR(S) : Hisato ITOH, et al.

It is certified that error appears in the above-indentified patent and that said Letters Patent is hereby corrected as shown below:

On the title page, Item [75], the fourth inventor's name should read:

--Tutomu Nishizawa--

Signed and Sealed this

Twenty-first Day of November, 1995

Attest:

BRUCE LEHMAN

*Attesting Officer*      *Commissioner of Patents and Trademarks*